(12) United States Patent
Saitoh et al.

(10) Patent No.: US 7,149,639 B2
(45) Date of Patent: Dec. 12, 2006

(54) METHOD OF DETECTING NOZZLE CLOGGING AND ANALYTICAL INSTRUMENT

(75) Inventors: Shin Saitoh, Tokyo (JP); Yoshiyuki Nakayama, White Plains, NY (US); Daisuke Kamuki, Saitama (JP); Kayoko Yamaya, Tokyo (JP)

(73) Assignee: Jeol Ltd., Tokyo (JP)

( * ) Notice: Subject to any disclaimer, the term of this patent is extended or adjusted under 35 U.S.C. 154(b) by 0 days.

(21) Appl. No.: 11/074,577

(22) Filed: Mar. 8, 2005

(65) Prior Publication Data

US 2005/0234673 A1 Oct. 20, 2005

(51) Int. Cl.
G01L 27/00 (2006.01)
G06F 19/00 (2006.01)

(52) U.S. Cl. ....................................................... 702/98
(58) Field of Classification Search ................. 702/45, 702/47, 50, 98, 100, 138; 347/6, 22, 89
See application file for complete search history.

(56) References Cited

U.S. PATENT DOCUMENTS 5,980,034 A * 11/1999 Tsai et al. ..................... 347/89

2003/0106314 A1 * 6/2003 Smith ........................ 60/449

FOREIGN PATENT DOCUMENTS

JP 09-015248 1/1997

* cited by examiner

Primary Examiner—Michael Nghiem
(74) Attorney, Agent, or Firm—The Webb Law Firm

(57) ABSTRACT

A method of detecting nozzle clogging by the use of threshold values that can be set easily is accomplished. Also, an analytical instrument equipped with a nozzle clogging detector using threshold values that can be set easily is accomplished. Threshold values corresponding to aspiration volumes of sample are calculated from plural threshold values (P1, P2, and P3) that have been set for discrete aspiration volumes (SV1, SV2, and SV3), respectively. The threshold values are found for each of plural aspiration programs corresponding to plural sets of conditions under which a sample is diluted, and for each of plural aspiration programs corresponding to plural kinds of samples. Threshold values are found for each of plural detection sensitivities.

10 Claims, 3 Drawing Sheets

METHOD OF DETECTING NOZZLE CLOGGING AND ANALYTICAL INSTRUMENT

BACKGROUND OF THE INVENTION

1. Field of the Invention

The present invention relates to a method of detecting nozzle clogging and to an analytical instrument. More specifically, the invention relates to a method of detecting clogging of a nozzle that draws in a sample and to an analytical instrument fitted with a device for detecting nozzle clogging.

2. Description of Related Art

In an automatic biochemical analyzer, a sample to be analyzed is drawn in by a nozzle and dispensed as aliquots. If the nozzle clogs up, the aspiration volume becomes inaccurate. Therefore, the nozzle is monitored at all times to detect whether the nozzle is clogged or not. The detection is done by comparing the nozzle pressure produced when the sample is drawn in with threshold values. See, for example, Japanese Patent Laid-Open No. 09-015248 (pages 3–4, FIG. 2).

The sample volume drawn in differs according to a different analytical item. The required aspiration pressure, i.e., the absolute value (hereinafter referred to as the nozzle pressure) of the differential pressure (normally, negative pressure) with the atmospheric pressure, differs according to a different aspiration volume. Therefore, it is necessary to prepare a different threshold value used for detection of nozzle clogging for each aspiration volume. Furthermore, even if the aspiration volume is constant, the required nozzle pressure varies depending on the degree of dilution of the sample and on the kind of sample. Consequently, it is also necessary to prepare a different threshold value for each set of dilution conditions and for each kind of sample. Moreover, if one attempts to make switchable the sensitivity at which clogging is detected, threshold values corresponding to plural sensitivities are necessary. To satisfy these requirements, required threshold values must all be preset. This needs a cumbersome and laborious operation.

SUMMARY OF THE INVENTION

Accordingly, it is an object of the present invention to achieve a method of detecting nozzle clogging in such a way that threshold values can be set easily. It is another object of the present invention to achieve an analytical instrument fitted with a device for detecting nozzle clogging in such a way that threshold values can be set easily.

A first embodiment of the present invention for solving the foregoing problems provides a method of detecting clogging of a nozzle, the method comprising the steps of: preparing aspiration programs for driving a pump appropriately depending on a sample to be split and dispensed as aliquots and on the amount of each aliquot; drawing in the sample according to any one of the programs; measuring the pressure inside the nozzle; and comparing the measured pressure with threshold values to detect whether the nozzle is clogged up. The threshold values corresponding to aspiration volumes of sample are calculated respectively by a method of calculation from plural threshold values which have been set for plural discrete aspiration volumes.

A second embodiment of the present invention is based on the first embodiment and further characterized in that the threshold values corresponding to the aspiration volumes of sample are found for the plural aspiration programs, respectively.

A third embodiment of the present invention is based on the second embodiment and further characterized in that the plural aspiration programs correspond to plural sets of conditions under which the sample is diluted.

A fourth embodiment of the present invention is based on the second embodiment and further characterized in that the plural aspiration programs correspond to plural kinds of samples.

A fifth embodiment of the present invention is based on any one of the first through fourth embodiments and further characterized in that sensitivity at which clogging is detected can be switched between plural values by setting plural threshold values for each aspiration volume, and that the threshold values corresponding to the aspiration volumes of sample are found for each of the plural values of the detection sensitivity.

A sixth embodiment of the present invention is based on any one of the first through fifth embodiments and further characterized in that the method of calculation uses at least one of linear interpolation, equations approximating higher-order functions, equations approximating logit log 1 function, logit log 2 function, and logit log 3 function, spline interpolation, and polygonal line approximation.

A seventh embodiment of the present invention provides an analytical instrument comprising: splitting-and-dispensing device for sample aspiration by a nozzle and dispensing the drawn sample as aliquots; detection device for detecting clogging of the nozzle by comparing pressure produced inside the nozzle when the sample is drawn in according to an aspiration program with threshold values, the program being used to drive a pump appropriately according to the sample to be split and dispensed and the amount of each aliquot; and analyzer device for analyzing the dispensed aliquots. The detection device includes calculation means for calculating threshold values corresponding to aspiration volumes of sample from plural threshold values set for each of plural discrete aspiration volumes.

An eighth embodiment of the present invention is based on the seventh embodiment and further characterized in that the calculation means finds the threshold values corresponding to the aspiration volumes of sample for each of plural aspiration programs.

A ninth embodiment of the present invention is based on the eighth embodiment and further characterized in that the plural aspiration programs correspond to plural sets of conditions under which the sample is diluted.

A tenth embodiment of the present invention is based on the eighth embodiment and further characterized in that the plural aspiration programs correspond to plural kinds of samples.

An eleventh embodiment of the present invention is based on any one of the seventh through tenth embodiments and further characterized in that sensitivity at which clogging is detected can be switched between plural values by setting plural threshold values for each aspiration volume, and that the calculation means finds the threshold values corresponding to the aspiration volumes of sample for each of the plural values of the detection sensitivity.

A twelfth embodiment of the present invention is based on any one of the seventh through eleventh embodiments and further characterized in that the calculation means utilizes at least one method selected from linear interpolation, equations approximating higher-order functions, equations approximating logit log 1 function, logit log 2 function, and logit log 3 function, spline interpolation, and polygonal line approximation.

In the first embodiment of the present invention, the threshold values corresponding to aspiration volumes of sample are calculated from plural threshold values set for each of plural discrete aspiration volumes. Therefore, a method of detecting nozzle clogging in such a way that the threshold values which can be set easily can be accomplished.

In the second embodiment of the present invention, the threshold values corresponding to the aspiration volumes of sample are found for each of plural aspiration programs. Therefore, a method of detecting nozzle clogging in such a way that the threshold values can be set easily for the plural aspiration programs can be accomplished.

In the third embodiment of the present invention, the plural aspiration programs correspond to the plural sets of conditions under which the sample is diluted. Therefore, a method of detecting nozzle clogging can be accomplished in such a way that the threshold values corresponding to the plural sets of dilution conditions can be set easily for the plural aspiration programs.

In the fourth embodiment of the present invention, the plural aspiration programs correspond to plural kinds of samples. Therefore, a method of detecting nozzle clogging can be accomplished in such a way that the threshold values corresponding to the kinds of samples can be set easily for the plural aspiration programs.

In the fifth embodiment of the present invention, plural threshold values are set for each aspiration volume. Thus, the sensitivity at which clogging is detected can be switched between plural values. Since the threshold values corresponding to the aspiration volumes of sample are found for each of the values of the detection sensitivity, a method of detecting nozzle clogging can be accomplished in such a way that the threshold values used for the plural values of the detection sensitivity can be set easily.

In the sixth embodiment of the present invention, the calculations are performed by at least one method selected from linear interpolation, equations approximating higher-order functions, equations approximating logit log 1 function, logit log 2 function, and logit log 3 function, spline interpolation, and polygonal line approximation. Therefore, a method of detecting nozzle clogging can be accomplished in such a way that the threshold values which are used for the plural aspiration programs corresponding to plural kinds of samples can be set easily.

In the seventh embodiment of the present invention, the detection device has the calculation means for calculating the threshold values corresponding to aspiration volumes of sample from the plural threshold values which have been set for the plural discrete aspiration volumes, respectively. Therefore, an analytical instrument equipped with a nozzle clogging detection device enabling easy setting of the threshold values can be accomplished.

In the eighth embodiment of the present invention, the calculation means finds the threshold values corresponding to the aspiration volumes of sample for each of plural aspiration programs. Therefore, an analytical instrument equipped with a nozzle clogging detection device enabling easy setting of the threshold values which are used for the aspiration programs can be accomplished.

In the ninth embodiment of the present invention, the plural aspiration programs correspond to the plural sets of conditions under which the sample is diluted. Therefore, an analytical instrument equipped with a nozzle clogging detection device enabling easy setting of the threshold values corresponding to the plural sets of dilution conditions for the aspiration programs can be accomplished.

In the tenth embodiment of the present invention, the plural aspiration programs correspond to plural kinds of samples. Therefore, an analytical instrument equipped with a nozzle clogging detection device enabling easy setting of the threshold values corresponding to the plural kinds of samples for the aspiration programs can be accomplished.

In the eleventh embodiment of the present invention, the sensitivity at which clogging is detected can be switched between plural values by setting plural threshold values for each aspiration volume. Since the calculation means finds the threshold values corresponding to the aspiration volume of sample for each of the values of the detection sensitivity, an analytical instrument equipped with a nozzle clogging detection device enabling easy setting of the threshold values for the plural values of the detection sensitivity can be accomplished.

In the twelfth embodiment of the present invention, the calculation means performs the calculations by at least one method selected from linear interpolation, equations approximating higher-order functions, equations approximating logit log 1 function, logit log 2 function, and logit log 3 function, and spline interpolation. Therefore, an analytical instrument equipped with a nozzle clogging detection device enabling easy detection of the threshold values for the plural values of the detection sensitivity can be accomplished.

Other objects and features of the present invention will appear in the course of the description thereof, which follows.

DESCRIPTION OF THE PREFERRED EMBODIMENTS

The preferred embodiments of the present invention are hereinafter described in detail with reference to the accompanying drawings. It is to be understood that the present invention is not limited to these embodiments. An automatic biochemical analyzer according to a preferred embodiment of the present invention is shown in the block diagram of FIG. 1. One example of preferred embodiment for carrying out the present invention regarding an analytical instrument is illustrated by the configuration of the present instrument. One example of preferred embodiment for carrying out the invention regarding a method of detecting nozzle clogging is illustrated by the operation of the present instrument.

Figure 1:
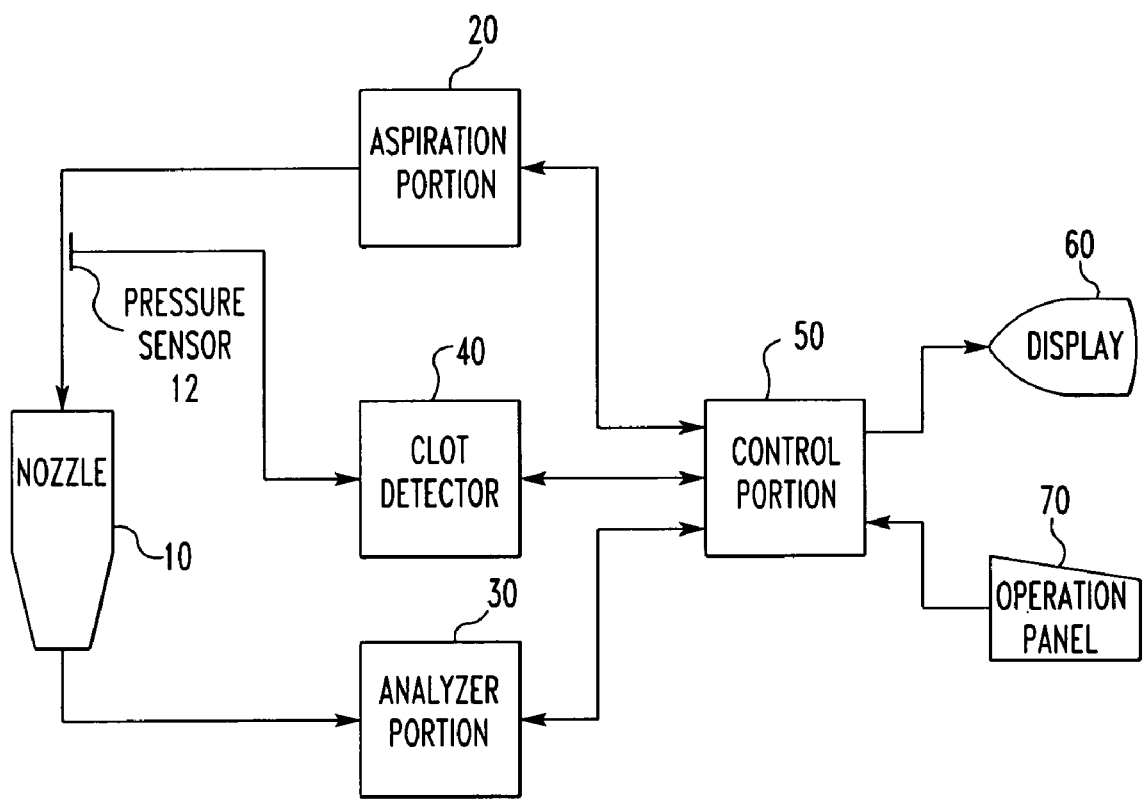
FIG. 1 is a block diagram of an automatic biochemical analyzer according to one embodiment of the present invention.

As shown in FIG. 1, the present analyzer has a nozzle 10 for taking in a sample to be analyzed. Negative pressure is supplied to the nozzle 10 from an aspiration portion or suction pump 20. Because of aspiration owing to the negative pressure, a given sample volume is drawn into the nozzle 10. The drawn sample is supplied to an analyzer portion 30, where the sample is analyzed. The portion consisting of the nozzle 10 and aspiration portion 20 is one example of a splitting-and-dispensing device of the present invention. The analyzer portion or analytical instrument 30 is one example of the analyzer device of the present invention.

The aspiration pressure of the nozzle 10 is detected by a pressure sensor 12. The absolute value of the aspiration pressure of the nozzle 10, i.e., the differential pressure with the atmospheric pressure (normally, negative pressure), is hereinafter referred to also as the nozzle pressure. A signal produced by detection of the nozzle pressure is entered into a clot detector 40. This detection portion or instrument 40 compares the nozzle pressure with a given threshold value and makes a decision as to whether the nozzle 10 is clogged or not. The threshold value used for the decision about clogging will be described in detail later. The clot detector 40 is one example of the detection device of the present invention.

The aspiration portion 20, analyzer portion 30, and clot detector 40 are controlled by a control portion 50, which controls the operation of the present instrument by sending and receiving signals to and from these various portions. The control portion 50 comprises a computer, for example.

The control portion 50 has a display 60 and an operation panel 70. The display 60 consists of a graphics display, for example, and displays information outputted from the control portion 50. The operation panel 70 consists of a keyboard, for example, and permits the user to enter various instructions and information into the control portion 50.

Threshold values used for making decisions about clogging are next described. One example of how the threshold values are set is graphed in FIG. 2. The coordinates in the graph are linearly scaled, semi-logarithmically scaled, or logarithmically scaled. As shown in the graph, the settable range of aspiration volume of sample lies from a minimum value of SVmin to a maximum value of SVmax. It is assumed that this range is divided into four subranges, for example. Aspiration volumes SV1, SV2, and SV3 indicating the boundaries between the subranges of aspiration volume are given. The user can arbitrarily set the aspiration volumes SV1, SV2, and SV3. Note that SVmin<SV1<SV2<SV3<SVmax. The number of the subranges is not limited to four. Any arbitrary number of subranges may be used. In the following example, the number of subranges is four. The same theory is applied to cases where the number of subranges is other than four.

Threshold values P1, P2, and P3 indicating the boundaries between ranges of pressure threshold values are given in a corresponding manner to the boundary aspiration volumes SV1, SV2, and SV3. The threshold values P1, P2, and P3 are negative values which can be set at will by the user. Their absolute values have the relation given by P1<P2<P3.

Combinations of the values of SV1, SV2, SV3 and P1, P2, P3 are determined for each aspiration program used to appropriately drive the pump according to the sample to be split and dispensed as aliquots and the amount of each aliquot. Where there are plural aspiration programs corresponding to plural dilution conditions for the same sample, combinations of the values of SV1, SV2, SV3 and P1, P2, P3 are set for each aspiration program. Where there are plural aspiration programs corresponding to plural kinds of samples, combinations of the values of SV1, SV2, SV3 and P1, P2, P3 are set for each aspiration program.

Figure 3:
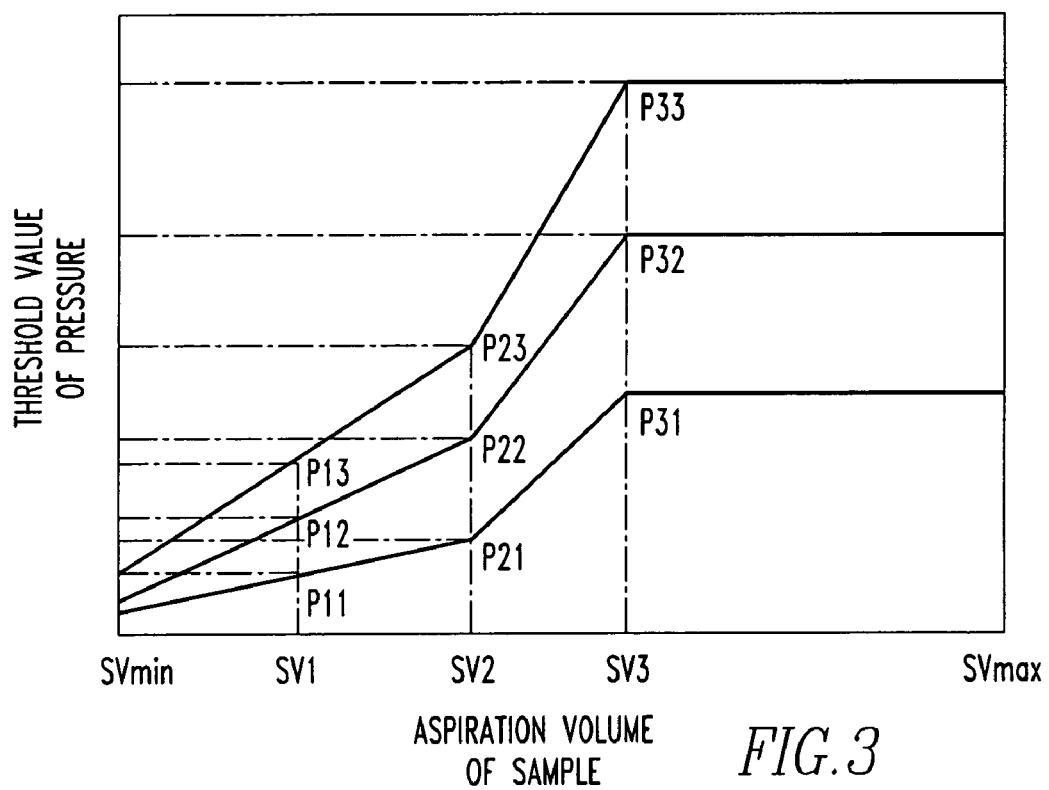
FIG. 3 is a graph illustrating one example of method of setting threshold values used for detection of clogging.

It is necessary to vary the clogging detection sensitivity according to the viscosity of the sample itself or the shape (lump or fibers) of the clogging substance (e.g., fibrin) within the sample. For this purpose, in a case where the clogging detection sensitivity can be switched between plural values (e.g., between three levels) by setting plural threshold values for each aspiration volume, three threshold values P11, P12, and P13 are set for the boundary aspiration volume SV1 as shown in FIG. 3. Three threshold values P31, P32, and P33 are set for the boundary aspiration volume SV2. Three threshold values P21, P22, and P23 are set for the boundary aspiration volume SV3. The amounts P1, P12, and P13 have a relation given by P11<P12<P13. Also, P21<P22<P23. Furthermore, P31<P32<P33.

The combination of the threshold values P11, P21, and P31 is used for high sensitivity. The combination of the threshold values P12, P22, and P32 is used for moderate sensitivity. The combination of the threshold values P13, P23, and P33 is used for low sensitivity.

Threshold values for aspiration volumes other than the boundary aspiration volumes SV1, SV2, and SV3 (i.e., aspiration volumes in the range between SVmin and SV1, aspiration volumes in the range between SV1 and SV2, aspiration volumes in the range between SV2 and SV3, and aspiration volumes in the range between SV3 and SVmax) are calculated from the boundary aspiration volumes SV1, SV2, and SV3 and from their threshold values P1, P2, and P3.

The calculations are performed by the clot detector 40, which is fitted with a calculation means such as a microprocessor. The detection portion finds the threshold values by the calculation function of the detection portion 40. This calculation function of the detection portion 40 is one example of the calculation means of the present invention.

The threshold values are computed, for example, by linear interpolation. In particular, the threshold values for the aspiration volumes between SVmin and SV1 and for the aspiration volumes between SV1 and SV2 are found by linear interpolation using the threshold values P1 and P2. The threshold value for the aspiration volumes between SV2 and SV3 is found by linear interpolation using the threshold values P2 and P3. The threshold value for the aspiration volumes between SV3 and SVmax is found by linear interpolation using the threshold value P3.

Figure 2:
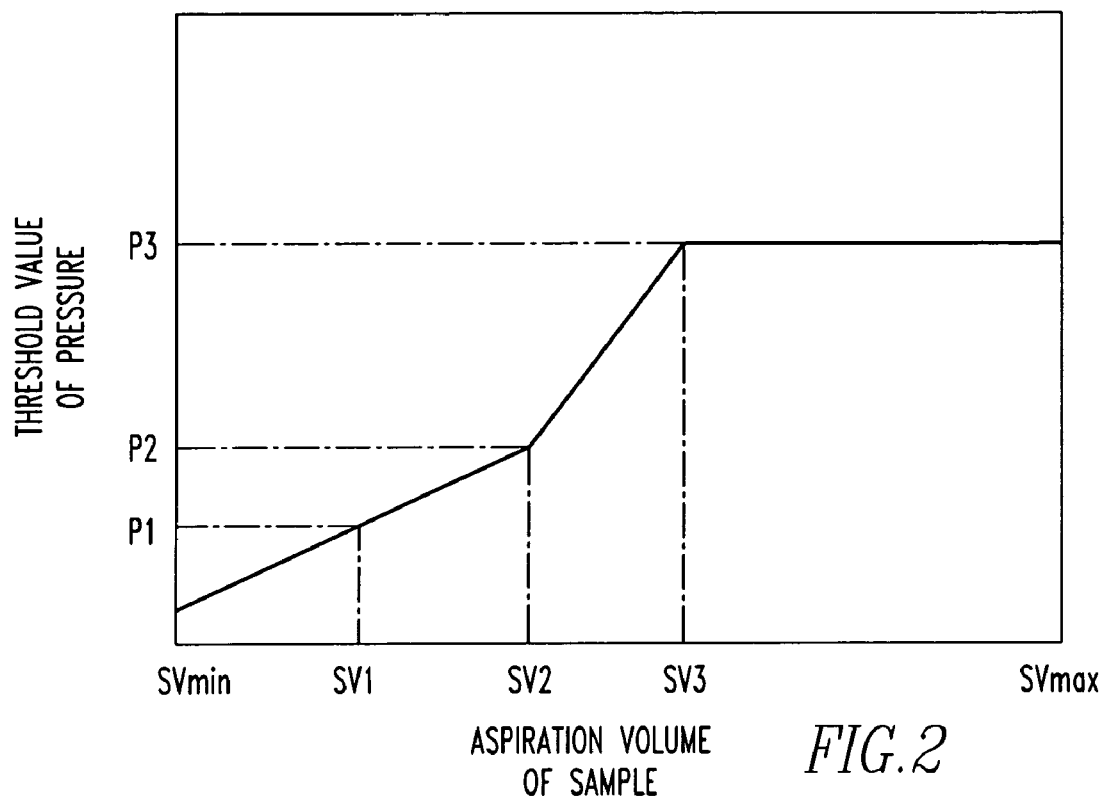
FIG. 2 is a graph illustrating one example of method of setting threshold values used for detection of clogging.

Thus, the threshold values for all the aspiration volumes from SVmin to SVmax are determined as in the polygonal line graph of FIG. 2. Furthermore, as shown in FIG. 3, the threshold values for the sensitivities for all the aspiration volumes from SVmin to SVmax are determined.

The method of finding the threshold values is not limited to linear interpolation techniques. Equations approximating functions of higher orders, such as second and third orders, equations approximating logit log 1, 2, 3 functions, spline correction equations, and any other approximate equation, can be used for the calculations. In addition, all of these methods of calculation may be prepared, and they may be appropriately selected in use.

Figure 4:
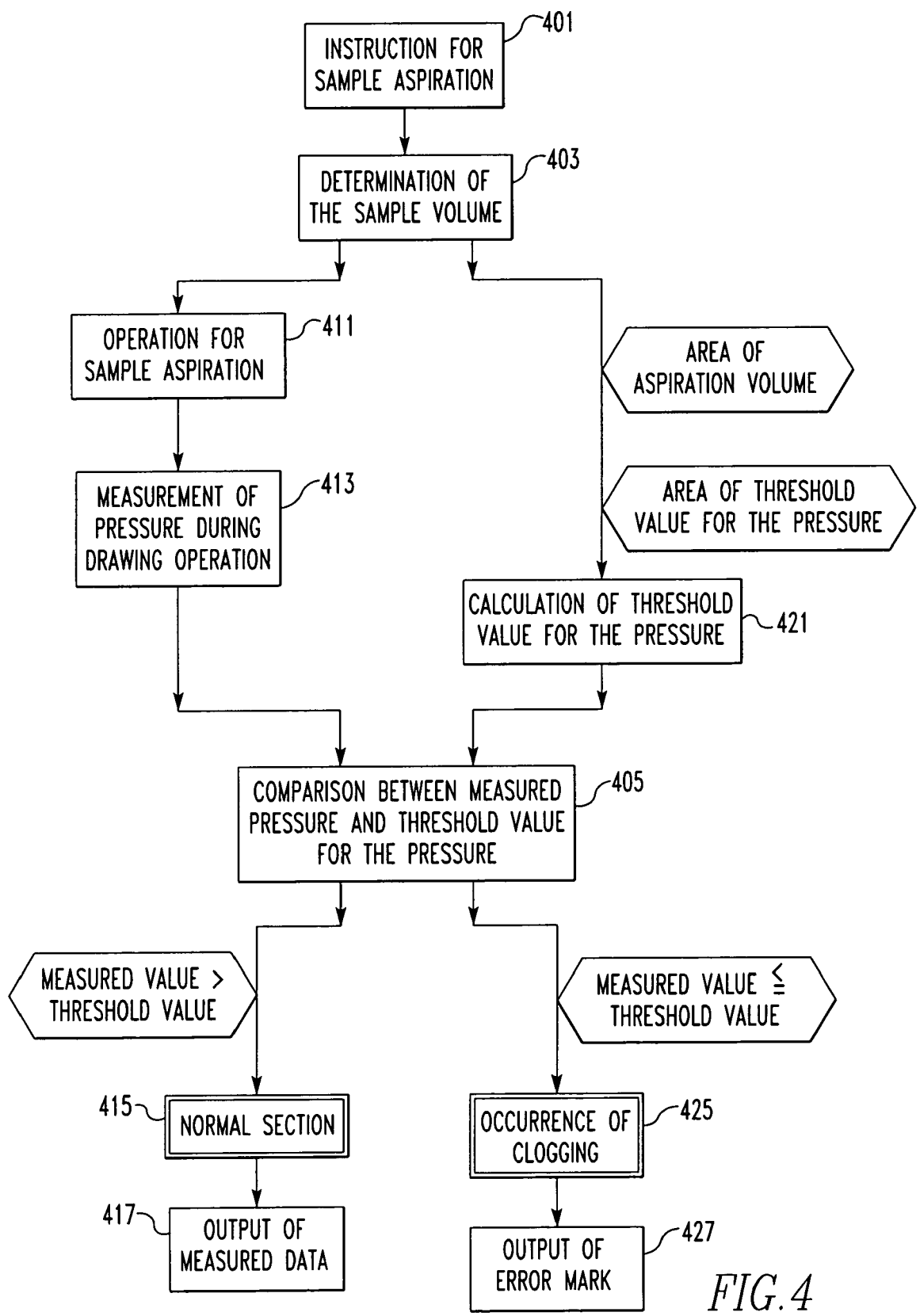
FIG. 4 is a flowchart illustrating a sequence of operations performed by an automatic biochemical analyzer.

The operation of the present analytical instrument is described by referring to the flowchart of FIG. 4. As shown in this flowchart, an instruction for sample aspiration is issued by the control portion 50 (step 401).

The amount of the sample drawn in is determined based on an aspiration program (step 403). This program is previously specified according to the kind of sample and the dilution condition.

An operation for drawing in the sample is performed (step 411). The pressure during this drawing operation is measured (step 413). That is, the output signal from the pressure sensor 12 is read during the drawing of the sample.

Concurrently with the operation for drawing in the sample and measurement of the pressure, the threshold value for the pressure is measured (step 421). For this purpose, the aspiration amount range and the pressure threshold value range to which the present aspiration volume belongs are discerned based on the aspiration volume of sample determined in step 403. Using the aspiration volumes indicative of the boundaries of the ranges and threshold values, threshold values used for clogging detection and corresponding to the determined aspiration volume are calculated. The calculations are performed using the aforementioned linear interpolation, equations approximating functions of higher orders such as second and third orders, equations approximating logit log 1 function, logit log 2 function, and logit log 3 function, spline interpolation, or polygonal line approximation.

The pressure actually measured is compared with the pressure threshold value (step 405). Where the actually measured pressure is greater than the threshold value, it is determined that the operation is a normal aspiration (step 415). The relation in magnitude between the actually measured value and the threshold value is a relation in magnitude between negative values. Therefore, their relation in magnitude in terms of absolute values is inverted. Since it is determined that the operation is a normal aspiration, the data (i.e., results of analysis) obtained by the measurement performed by the analyzer portion 30 is outputted (step 417).

Where "the actually measured value≦the threshold value", it is determined that clogging has occurred (step 425). It is to be noted that the relation in magnitude between the actually measured value and the threshold value is a relation in magnitude in terms of negative values. Therefore, the relation in magnitude in terms of absolute values is reversed. Since it has been determined that clogging has taken place, a mark indicating error is outputted (step 427) by attaching the error mark to the measurement data. This calls the user's attention to incompleteness of the measurement data.

As described so far, threshold values used for detection of clogging are found by calculations which use the aspiration volumes threshold values stipulating an aspiration amount interval or range to which the present aspiration volume of sample belongs as well as the threshold values, according to the aspiration amount range and pressure value range. Therefore, it is not necessary to preset threshold values for all the aspiration volumes. In addition, those threshold values which need to be preset are only the aspiration volumes stipulating the boundaries of the ranges and threshold values. Consequently, a method of detecting nozzle clogging in such a way that threshold values can be set easily can be accomplished. Also, an analytical instrument equipped with a nozzle clogging detection device enabling easy setting of threshold values can be accomplished.

Having thus described our invention with the detail and particularity required by the Patent Laws, what is desired protected by Letters Patent is set forth in the following claims.

The invention claimed is:

1. A method of detecting clogging of a nozzle used for aspirating and dispensing aliquot volumes of a sample, comprising the steps of:
preparing an aspiration program consisting of threshold pressure values and corresponding plural discrete aspiration volumes depending on a sample to be dispensed wherein sensitivity at which clogging is detected is switched between plural values by setting plural threshold values for each aspiration volume, and wherein the threshold values corresponding to the aspiration volumes of sample are found for each of said plural values of the sensitivity;
driving an aspiration pump to draw the sample according to the program;
measuring the pressure inside the nozzle; and
comparing the measured pressure with threshold values which correspond to aspiration volumes of sample and which are calculated by a method of interpolation from plural threshold values set for plural discrete aspiration volumes, to detect whether the nozzle is clogged or not and indicating the result.

2. A method of detecting clogging of a nozzle as set forth in claim 1, wherein the threshold values corresponding to said aspiration volumes of sample are found for each of plural aspiration programs.

3. A method of detecting clogging of a nozzle as set forth in claim 2, wherein said plural aspiration programs correspond to plural sets of conditions under which the sample is diluted.

4. A method of detecting clogging of a nozzle as set forth in claim 2, wherein said plural aspiration programs correspond to plural kinds of samples.

5. A method of detecting clogging of a nozzle as set forth in claim 1, wherein said method of calculation uses at least one selected from linear interpolation, equations approximating higher-order functions, equations approximating logit log 1 function, logit log 2 function, and logit log 3 function, spline interpolation, and polygonal line approximation.

6. An analytical instrument used for aspirating and dispensing aliquot volumes of a sample comprising:
splitting-and-dispensing means for sample aspiration by a nozzle and dispensing the drawn sample as aliquots;
detection means for detecting clogging of the nozzle by comparing pressure produced inside the nozzle when the sample is drawn in according to an aspiration program consisting of threshold pressure values and corresponding plural discrete aspiration volumes, the program being used to drive an aspirating pump appropriately according to the sample to be dispensed and the amount of each aliquot volume wherein sensitivity at which clogging is detected can be switched between plural values by selling plural threshold values for each aspiration volume, and wherein the threshold values corresponding to said aspiration volumes of sample are found for each of said plural values of the sensitivity;
analyzer means for analyzing the aliquots of sample;
calculation means included in said detection means and acting to interpolate threshold values corresponding to aspiration volumes of sample from plural threshold values set for each of plural discrete aspiration; and
means for indicating a detected clogging result.

7. An analytical instrument as set forth in claim 6, wherein said calculation means finds the threshold values corresponding to said aspiration volumes of sample for each of plural aspiration programs.

8. An analytical instrument as set forth in claim 7, wherein said plural aspiration programs correspond to plural sets of conditions under which the sample is diluted.

9. An analytical instrument as set forth in claim 7, wherein said plural aspiration programs correspond to plural kinds of samples.

10. An analytical instrument as set forth in claim 6, wherein said calculation means utilizes at least one method selected from linear interpolation, equations approximating higher-order functions, equations approximating logit log 1function, logit log 2 function, and logit log 3 function, spline interpolation, and polygonal line approximation.

* * * * *

UNITED STATES PATENT AND TRADEMARK OFFICE
CERTIFICATE OF CORRECTION

PATENT NO. : 7,149,639 B2  
APPLICATION NO. : 11/074577  
DATED : December 12, 2006  
INVENTOR(S) : Saitoh et al.

It is certified that error appears in the above-identified patent and that said Letters Patent is hereby corrected as shown below:

Title page, item, Insert  
-- (30)    Foreign Application Priority Data  
March 8, 2004    JP    ..................................2004-63403 --

<u>Column 8</u>, Line 31, Claim 6, "by selling plural" should read -- by setting plural --

<u>Column 8</u>, Line 40, Claim 6, "aspiration; and" should read -- aspiration volumes; and --

Signed and Sealed this

Twenty-fourth Day of April, 2007

JON W. DUDAS  
*Director of the United States Patent and Trademark Office*